United States Patent
Huo et al.

(10) Patent No.: US 11,158,050 B2
(45) Date of Patent: Oct. 26, 2021

(54) BONE SUPPRESSION FOR CHEST RADIOGRAPHS USING DEEP LEARNING

(71) Applicant: CARESTREAM HEALTH, INC., Rochester, NY (US)

(72) Inventors: Zhimin Huo, Pittsford, NY (US); Hui Zhao, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 75 days.

(21) Appl. No.: 16/535,124

(22) Filed: Aug. 8, 2019

(65) Prior Publication Data

US 2020/0051245 A1    Feb. 13, 2020

Related U.S. Application Data

(60) Provisional application No. 62/717,163, filed on Aug. 10, 2018.

(51) Int. Cl.
*G06T 7/00* (2017.01)
*A61B 6/00* (2006.01)

(52) U.S. Cl.
CPC .......... *G06T 7/0014* (2013.01); *A61B 6/5252* (2013.01); *G06T 7/97* (2017.01); *G06T 2207/10116* (2013.01); *G06T 2207/20081* (2013.01); *G06T 2207/20084* (2013.01); *G06T 2207/30008* (2013.01)

(58) Field of Classification Search
CPC ............... A61B 6/4441; A61B 6/5252; G06T 2207/10116; G06T 2207/20081; G06T 2207/20084; G06T 2207/30008; G06T 5/005; G06T 7/0014; G06T 7/97
See application file for complete search history.

(56) References Cited

U.S. PATENT DOCUMENTS

| | | | |
|---|---|---|---|
| 2009/0087070 A1* | 4/2009 | Slabaugh | G06T 5/20 382/132 |
| 2014/0243579 A1* | 8/2014 | Roeske | A61B 6/485 600/1 |

OTHER PUBLICATIONS

Yang, Wei, et al. "Cascade of multi-scale convolutional neural networks for bone suppression of chest radiographs in gradient domain." Medical image analysis 35 (2017): 421-433. (Year: 2017).*
Gusarev, Maxim, et al. "Deep learning models for bone suppression in chest radiographs." 2017 IEEE Conference on Computational Intelligence in Bioinformatics and Computational Biology (CIBCB). IEEE, 2017 (Year: 2017).*

* cited by examiner

Primary Examiner — Leon Viet Q Nguyen

(57) ABSTRACT

A system and method for generating a rib suppressed radiographic image using deep learning computation. The method includes using a convolutional neural network module trained with pairs of a chest x-ray image and its counterpart bone suppressed image. The bone suppressed image is obtained using a bone suppression algorithm applied to the chest x-ray image. The convolutional neural network module is then applied to a chest x-ray image or the bone suppressed image to generate an enhanced bone suppressed image.

7 Claims, 11 Drawing Sheets

BONE SUPPRESSION FOR CHEST RADIOGRAPHS USING DEEP LEARNING

CROSS REFERENCE TO RELATED APPLICATIONS

This application claims priority to U.S. Patent Application Ser. No. 62/717,163, filed Aug. 10, 2018, in the name of Huo et al., and entitled BONE SUPPRESSION FOR CHEST RADIOGRAPHS USING DEEP LEARNING MODELS, which is hereby incorporated by reference herein in its entirety.

This application is related in certain respects to U.S. Pat. No. 8,913,817, issued Dec. 16, 2014, in the name of Huo et al., entitled RIB SUPPRESSION IN RADIOGRAPHIC IMAGES; U.S. Pat. No. 9,269,139, issued Feb. 23, 2016, in the name of Huo et al., entitled RIB SUPPRESSION IN RADIOGRAPHIC IMAGES; U.S. Pat. No. 9,659,390, issued May 23, 2017, in the name of Huo et al., entitled TOMOSYNTHESIS RECONSTRUCTION WITH RIB SUPPRESSION; U.S. Pat. No. 9,668,712, issued Jun. 6, 2017, in the name of Foos et al., entitled METHOD AND SYSTEM FOR QUANTITATIVE IMAGING; and U.S. Pat. No. 8,961,011, issued Feb. 24, 2015, in the name of Lalena, entitled MOBILE RADIOGRAPHY UNIT HAVING MULTIPLE MONITORS; all of which are hereby incorporated by reference as if fully set forth herein in their entirety.

BACKGROUND OF THE INVENTION

The disclosure relates generally to the field of medical imaging, and in particular to bone suppression for chest radiographs. More specifically, the disclosure relates to a method of bone suppression for chest radiographs using deep learning convolutional networks, and program modules for executing such deep learning convolutional algorithms.

BRIEF DESCRIPTION OF THE INVENTION

A system and method for generating a rib suppressed radiographic image using deep learning computation. The method includes using a convolutional neural network module trained with pairs of a chest x-ray image and its counterpart bone suppressed image, or, in other words, pairs of radiographic images including a starting image and a target image. The bone suppressed image is obtained using a known bone suppression algorithm applied to the chest x-ray image. A known convolutional neural network module trained to suppress rib content is then applied to a chest x-ray image or the bone suppressed image to generate an enhanced bone suppressed chest x-ray image.

In one embodiment, a system includes an x-ray imaging system to capture a radiographic image. A processor is configured to apply a bone suppression algorithm to the captured radiographic image to generate a bone suppressed version of the captured radiographic image. A trained deep learning module is trained by both the captured radiographic image and the bone suppressed version of the captured radiographic image to generate an enhanced bone suppressed image of the radiographic image.

In one embodiment, a system includes electronic memory for storing a radiographic image. A processor is configured to apply a bone suppression algorithm to the stored radiographic image to generate a bone suppressed version of the stored radiographic image. A deep learning module receives the stored radiographic image and the bone suppressed version of the stored radiographic image. The deep learning module is configured to be trained on the images to generate an enhanced bone suppressed image using the stored radiographic image.

In one embodiment, a system includes an x-ray imaging system to capture a current radiographic image. A deep learning module trained on a plurality of previously captured radiographic images and a corresponding plurality of bone-suppressed radiographic images generated from the plurality of previously captured radiographic images. A processor of the system is configured to apply the trained deep learning module to the captured current radiographic image to generate an enhanced bone-suppressed radiographic image.

In one embodiment, a method includes receiving a digital radiographic image and applying a bone suppression algorithm to the received digital radiographic image to generate a digital bone suppressed radiographic image. A deep learning neural network module trained for suppressing bone regions of digital radiographic images is accessed to generate an enhanced digital bone suppressed radiographic image using the received digital radiographic image.

In one embodiment, a method includes receiving a digital radiographic image and applying a bone suppression algorithm to the received digital radiographic image to generate a digital bone suppressed radiographic image. A deep learning neural network module trained for suppressing bone regions of digital radiographic images is accessed to generate an enhanced digital bone suppressed radiographic image using the generated digital bone suppressed radiographic image.

In one embodiment, a computer implemented method includes acquiring a digital radiographic image, applying a bone suppression algorithm to the acquired radiographic image to generate a bone suppressed radiographic image. A convolutional neural network module trained using a plurality of radiographic training images is applied to the bone suppressed radiographic image or the acquired digital radiographic image to generate an enhanced bone suppressed radiographic image.

In at least one arrangement, there is provided an x-ray imaging system to capture a medical image, a deep learning module, and a processor applying a bone suppression algorithm to the captured medical image, and applying the deep learning module to the bone suppressed captured medical image to generate an enhanced bone suppressed image.

In at least one arrangement, there is provided an x-ray imaging system to capture a medical image, a deep learning module trained using a plurality of medical images and a plurality of bone-suppressed images. A processor applies the trained deep learning module to the captured medical image to generate an enhanced medical image.

In at least one arrangement, there is provided an x-ray imaging system to capture a medical image, a deep learning module trained using a plurality of medical images and a plurality of bone-suppressed images derived from at least some of the plurality of medical images, and a processor to apply the trained deep learning module to the captured medical image to generate an enhanced medical image.

In at least one arrangement, there is provided a method including the steps of acquiring a digital medical image using an x-ray projection imaging system, applying a bone suppression algorithm to the medical image to generate a bone suppressed image, providing a deep learning convolutional neural network module trained using a plurality of medical images, applying the neural network module to the bone suppressed image to generate an enhanced bone suppressed image, and displaying, storing, or transmitting the enhanced bone suppressed image.

In at least one arrangement, there is provided a method including the steps of acquiring a digital medical image using an x-ray imaging system, applying a bone suppression algorithm to the medical image to generate a bone suppressed image, providing a plurality of training images, providing a convolutional neural network module trained using at least some of the plurality of training images, applying the convolutional neural network module to a bone suppressed image to generate an enhanced bone suppressed image, and displaying, storing, or transmitting the enhanced bone suppressed image.

In at least one method the steps include providing a plurality of training images including providing a plurality of digital medical images and providing a plurality of bone-suppressed images derived from at least some of the plurality of digital medical images.

In at least one method, providing the plurality of training images includes providing a plurality of chest x-ray images and a plurality of rib suppressed chest x-ray images.

In at least one method, providing the plurality of training images includes providing (i) a plurality of chest x-ray images and (ii) a plurality of bone suppressed chest x-ray images derived from the plurality of chest x-ray images.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE EMBODIMENTS

Figure 1:
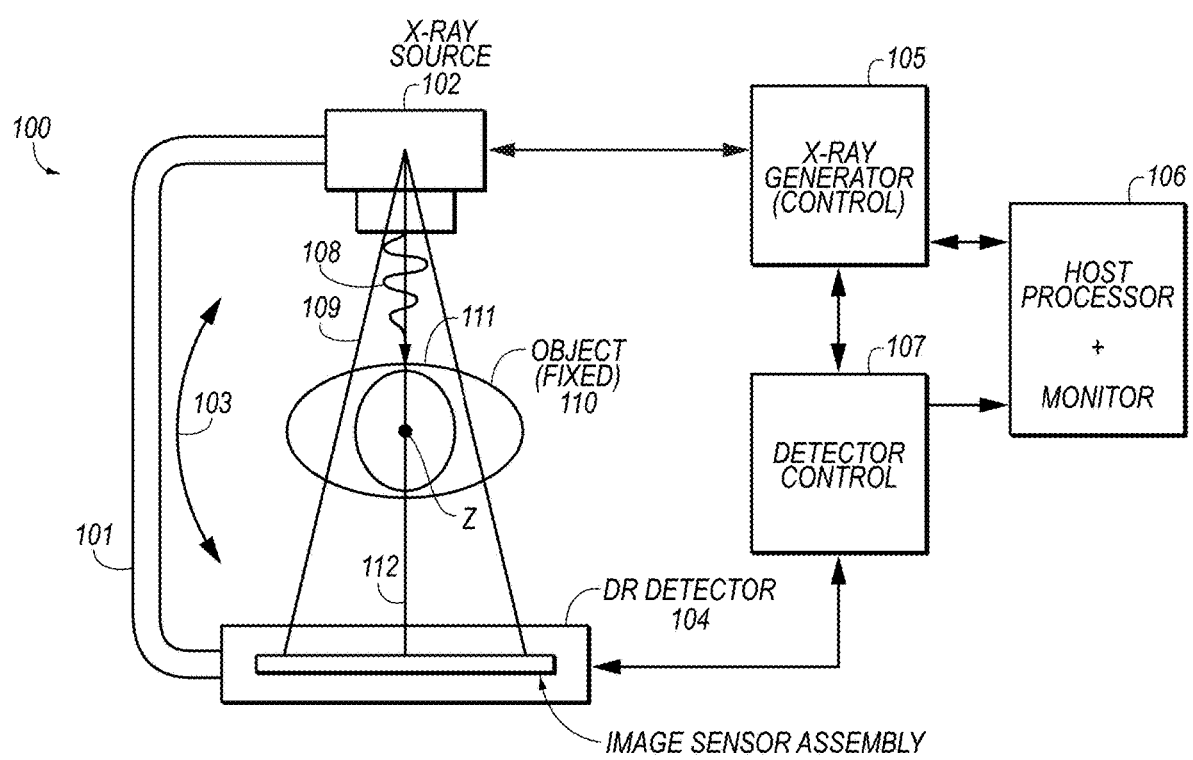
FIG. 1 is a schematic diagram of an exemplary x-ray imaging system.

FIG. 1 is a schematic diagram of an exemplary digital radiographic (DR) imaging system 100 that may be used to practice embodiments of the present invention disclosed herein. The DR imaging system 100 includes an x-ray source 102 configured to generate radiographic energy. The x-ray source 102 may include a single x-ray source or it may include multiple x-ray sources. The imaging system 100 further includes a generally planar DR detector 104, although a curved detector may also be used. A computer system 106 having a processor, electronic memory, and digital monitor configured to display images captured by the DR detector 104 is electrically connected to the x-ray source 102 and DR detector 104. The DR detector 104 may include a two dimensional array of photosensor cells arranged in electronically addressable rows and columns. The DR detector 104 may be positioned to receive x-rays 108 passing through an object 110, such as a human patient, during radiographic energy exposures, or radiographic firing of energy pulses, as emitted by the x-ray source 102 during an imaging procedure. As shown in FIG. 1, the radiographic imaging system 100 may use an x-ray source 102 that emits collimated x-rays 108, e.g. a directed x-ray beam 109 such as a cone beam having a field of view, selectively aimed at and passing through a preselected region 111 of the object 110. The x-ray beam 109 may be attenuated by varying degrees along its plurality of rays according to the internal 3D structure of the object 110, whereby the attenuated rays are detected by the array of photosensitive cells in DR detector 104. The DR detector 104 is positioned, as much as possible, in a perpendicular relation to a substantially central path 112 of the plurality of rays 108 emitted by the x-ray source 102. The array of photosensitive cells (pixels) of DR detector 104 may be electronically read out (scanned) by their position according to column and row. As used herein, the terms "column" and "row" refer to the vertical and horizontal arrangement of the photosensor cells and, for clarity of description, it will be assumed that the rows extend horizontally and the columns extend vertically. However, the orientation of the columns and rows is arbitrary and does not limit the scope of any embodiments disclosed herein. Furthermore, the term "object" may be illustrated as a human patient in the description of FIG. 1, however, an object of a DR imaging system 100 or 100, as the term is used herein, may be a human or an animal.

In one exemplary embodiment, the photosensitive cells of DR detector 104 may be read out to capture one or a plurality of projection images under control of a detector control circuit 107 so that the exposure data (digital images) from the array of detector 104 may be transmitted to the computer system 106. Each photosensitive cell in the DR detector 104 may independently detect and store an attenuation value which is generated by a charge level generated in proportion to an intensity, or energy level, of the attenuated radiographic radiation, or x-rays, received and absorbed in the photosensitive cells. Thus, each photosensitive cell, when read-out, provides information, or an attenuation value, defining a pixel of a radiographic image that may be digitally decoded by image processing electronics in the computer system 106 and displayed by the monitor for viewing by a user. Image processing electronics may be included within the DR detector 104 housing, whereby the radiographic images may be relayed to a computer system 106 by cable or wirelessly via electromagnetic wave transmission. As shown in FIG. 1, the source 102 and DR detector 104 may be affixed to an exemplary stationary C-arm 101, or a rotating mechanism controlling such C-arm 101 and configured to revolve the source 102 and detector 104 in either of the angular directions indicated by the arrow 103 about an imaging axis z that coincides with the object 110 while the DR detector captures a plurality of radiographic projection images of the object 110 at a number of angular imaging positions as the C-arm rotates about the object 110.

The computer system 106 includes a processor and electronic memory and may communicate with a detector control circuit 107 and x-ray generator 104 over a connected cable (wired) or, as described herein, the DR detector 104 may be equipped with a wireless transmitter to transmit radiographic image data wirelessly to the computer system 106 for image processing therein. The detector control 107 may also include a processor and electronic memory (not shown) to control operations of the DR detector 104 as described herein, or such control operations may be implemented using the computer system 106 by use of programmed instructions. Programmed instructions stored in memory accessible to computer system 106 may be executed to perform the reconstruction algorithms described herein. The computer system may also be used to control activation of the x-ray generator 105 and the x-ray source 102 during a radiographic exposure, or scan, controlling an x-ray tube electric current magnitude, and thus the fluence of x-rays in x-ray beam 109, and/or the x-ray tube voltage, and thus the energy level of the x-rays in x-ray beam 109.

The DR detector 104 may transmit image (pixel) data to the monitor computer system 106 based on the radiographic exposure data received from its array of photosensitive cells. Alternatively, the DR detector may be equipped to process the image data and store it, or it may store raw unprocessed image data, in local or remotely accessible memory. The photosensitive cells in DR detector 104 may each include a sensing element sensitive to x-rays, i.e. it directly absorbs x-rays and generates an amount of charge carriers in proportion to a magnitude of the absorbed x-ray energy. A switching element may be configured to be selectively activated to read out the charge level of a corresponding x-ray sensing element. Alternatively, photosensitive cells of the indirect type may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, is disposed over the light sensitive sensing elements to convert incident x-ray radiographic energy to visible light energy. Thus, it should be noted that the DR detector 104, in the embodiments disclosed herein, may include an indirect or direct type of DR detector.

In one embodiment, the photosensitive cell array may be read out by sequentially switching rows of the photosensitive array to a conducting (on) state by means of read-out circuits. This digital image information may be subsequently processed by computer system 106 to yield a digital projection image which may then be digitally stored and immediately displayed on a monitor, or it may be displayed at a later time by accessing the digital electronic memory containing the stored image. A projection images captured and transmitted by the detector 104 may be accessed by computer system 106 to generate a bone suppressed image using algorithms as described herein. The flat panel DR detector 104 having an imaging array as described herein is capable of both single-shot (e.g., static, projection) and continuous image acquisition.

One embodiment of the computer system 106 further includes various software modules and hardware components to be implemented for generating a bone suppressed radiographic image using the methods described herein. According to one aspect of the current invention, bone suppressed images are generated using cone beam radiographic image data.

Figure 2:
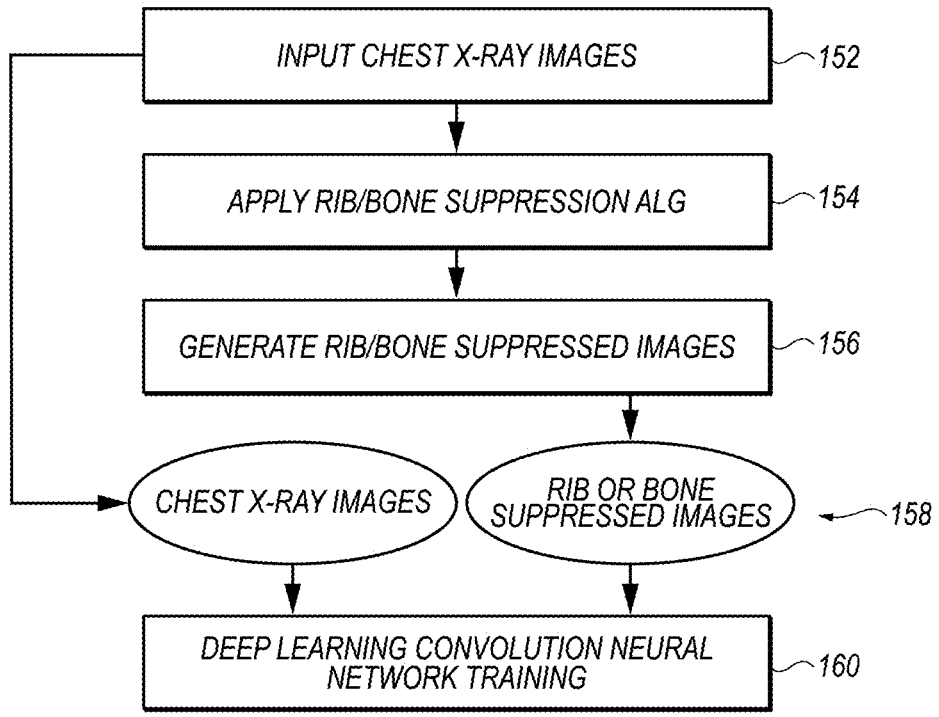
FIGS. 2-2D are flowcharts in accordance with the present disclosure.
Figure 2:
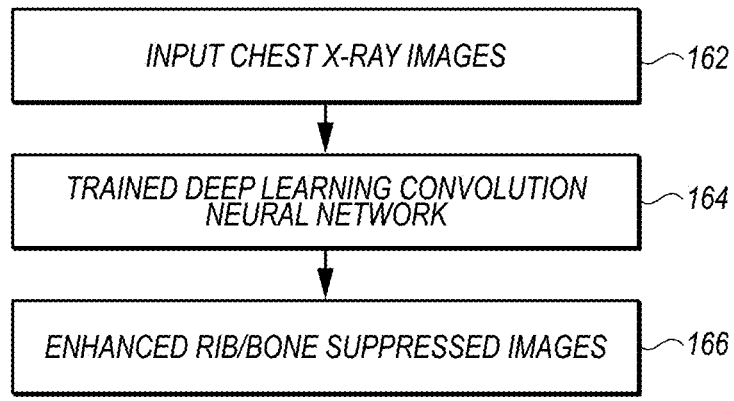

Referring to FIG. 2, there is shown a flowchart in accordance with one embodiment of the present disclosure. As illustrated, the method includes step 152 wherein a medical radiographic image such as a digital chest X-ray image (FIG. 6A) is accessed, received, as by digital transmission, or captured using an x-ray system 100 as described herein. At step 154, a rib or bone suppression algorithm is applied to the radiographic image so as to suppress ribs or bone structures in the image, as illustrated herein below. The resulting radiographic image is a rib or bone suppressed radiographic image (FIG. 6B) generated at step 156. At step 158, the original captured chest x-ray image, e.g. starting image, and its counterpart bone-suppressed image, e.g., target image, are input to a deep learning convolution neural network module, which are used by the network module for training purposes at step 160. The training steps 152-160 may be repeated a finite number of times.

At step 162, a medical radiographic image such as a digital chest X-ray image is provided to the trained deep learning convolution neural network which, at step 164, applies its learned algorithm, via the training procedure, to suppress bony structures in the provided medical radiographic image to generate, at step 166, an enhanced bone-suppressed radiographic image derived from the provided medical radiographic image.

Preferably, the training of the deep learning module involves many pairs of chest x-ray images (starting images) and their counterpart bone suppressed x-ray images (target images) using known bone suppression algorithms such as those in the prior art incorporated herein by reference. The module, or model, is trained to generate an output radiographic image that is rib free, similar to the target bone suppressed image generated from each input chest x-ray image. Each of the bone suppressed radiographic images are preferably derived directly from its associated original radiographic projection chest image using the known bone suppression algorithms. In a preferred embodiment, the bone suppressed images are not derived using previous approaches whereby a radiographic subtraction procedure is applied or using other manipulations of two images. For example, in other previous systems, a pair of x-ray images may be obtained using two exposures of a patient at two different x-ray source energies in a dual energy x-ray imaging system, wherein one of the two energies is less sensitive to bony structures. Thus, the present invention does not require multiple exposures at any stage of its generation of bone suppressed images, including the training stage as illustrated in FIG. 2. That is, no intermediate radiographic image is generated—the bone suppressed image is generated directly from an original projection chest x-ray image. As such, Applicants have recognized that for the methods described herein, the bone suppressed images are preferably derived directly from radiographic chest images via the bone suppression algorithm, radiographic image manipulation or radiographic image filtering. Examples of such known algorithms, image manipulation or image filtering are described in the three prior art references to Huo incorporated herein. Applicants refer herein to well known bone suppression algorithms and do not further describe details of such algorithms.

In one embodiment, another known technology using convolutional neural networks (CNN) or Generative Adversarial Networks (GANs) as deep learning modules, or models, may be trained to suppress bony structures in radiographic images. The deep learning CNN module is comprised of a library of training images, particularly a plurality of image pairs, for example: a chest x-ray image (starting image) and its corresponding counterpart bone suppressed image (target). In a preferred arrangement, the deep learning module is trained using a plurality of radiographic images and a plurality of bone-suppressed radiographic images derived from at least some of the plurality of starting radiographic images.

In machine learning, the CNN is a class of deep, feed-forward artificial neural networks, often applied to analyzing visual imagery. CNNs use a variation of multilayer perceptrons, or processing elements, designed to require minimal preprocessing. Convolutional networks were inspired by biological processes in that the connectivity pattern between neurons resembles the organization of an animal visual cortex. In one embodiment, the present disclosure describes herein below using GANs to suppress ribs in radiographic images in FIG. 3.

Figure 2A:
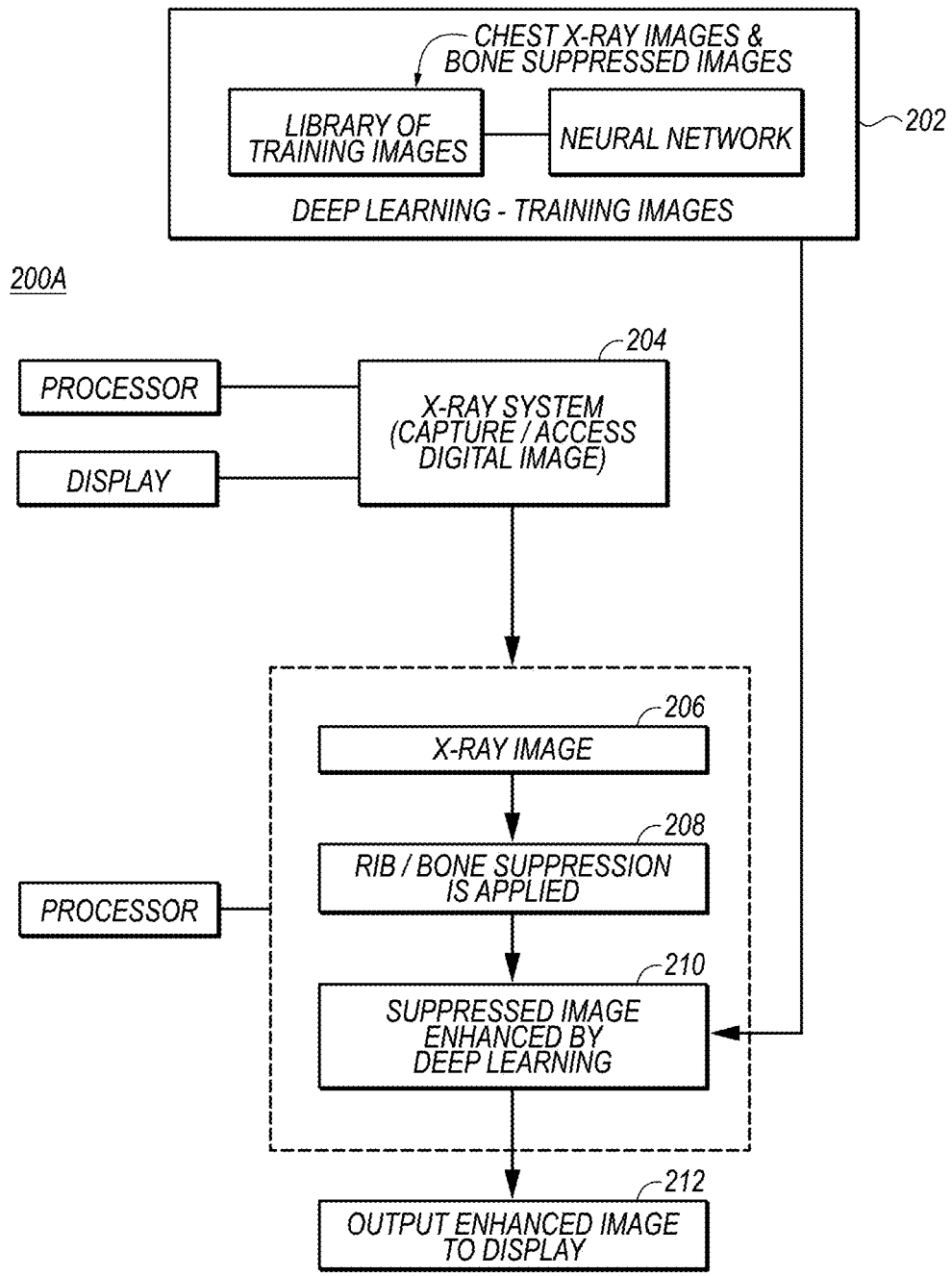

Referring now to the flow charts of FIGS. 2A-2D, there are shown alternative methods for the method of FIG. 2. FIG. 2A illustrates an exemplary x-ray imaging system 200A, which may resemble the x-ray imaging system of FIG. 1 in certain respects, wherein a library of training images comprising pairs of original captured radiographic images and corresponding bone suppressed radiographic images, derived directly from the original captured radiographic images, are stored in digital electronic memory 202. The x-ray imaging system 200A also includes a neural network module stored in the digital electronic memory 202 which is available for applying a learned bone suppression algorithm to radiographic images. The learned bone suppression algorithm may be applied to radiographic images captured by the x-ray imaging system 200A or to radiographic images captured elsewhere and provided to the x-ray imaging system 200A such as by providing access to electronic memory containing the radiographic images to be bone suppressed or by transmitting the radiographic images to the x-ray imaging system 200A. The neural network module may be trained using the library of training images. The x-ray imaging system 200A includes a processing system 204 having a processor, digital memory, and a display for displaying radiographic images. The processor may be programmable to apply a conventional bone suppression algorithm, as disclosed in the patents incorporated herein by reference, to radiographic images. The processor may be programmed to access a non-bone suppressed radiographic image 206 and to apply the conventional bone suppression algorithm 208 thereto. The processor may be programmed to apply the bone suppression algorithm learned by the neural network to the conventionally bone suppressed radiographic image 208 to generate an enhanced bone suppressed radiographic image 210 which is then capable of being output to the display 212.

Figure 2B:
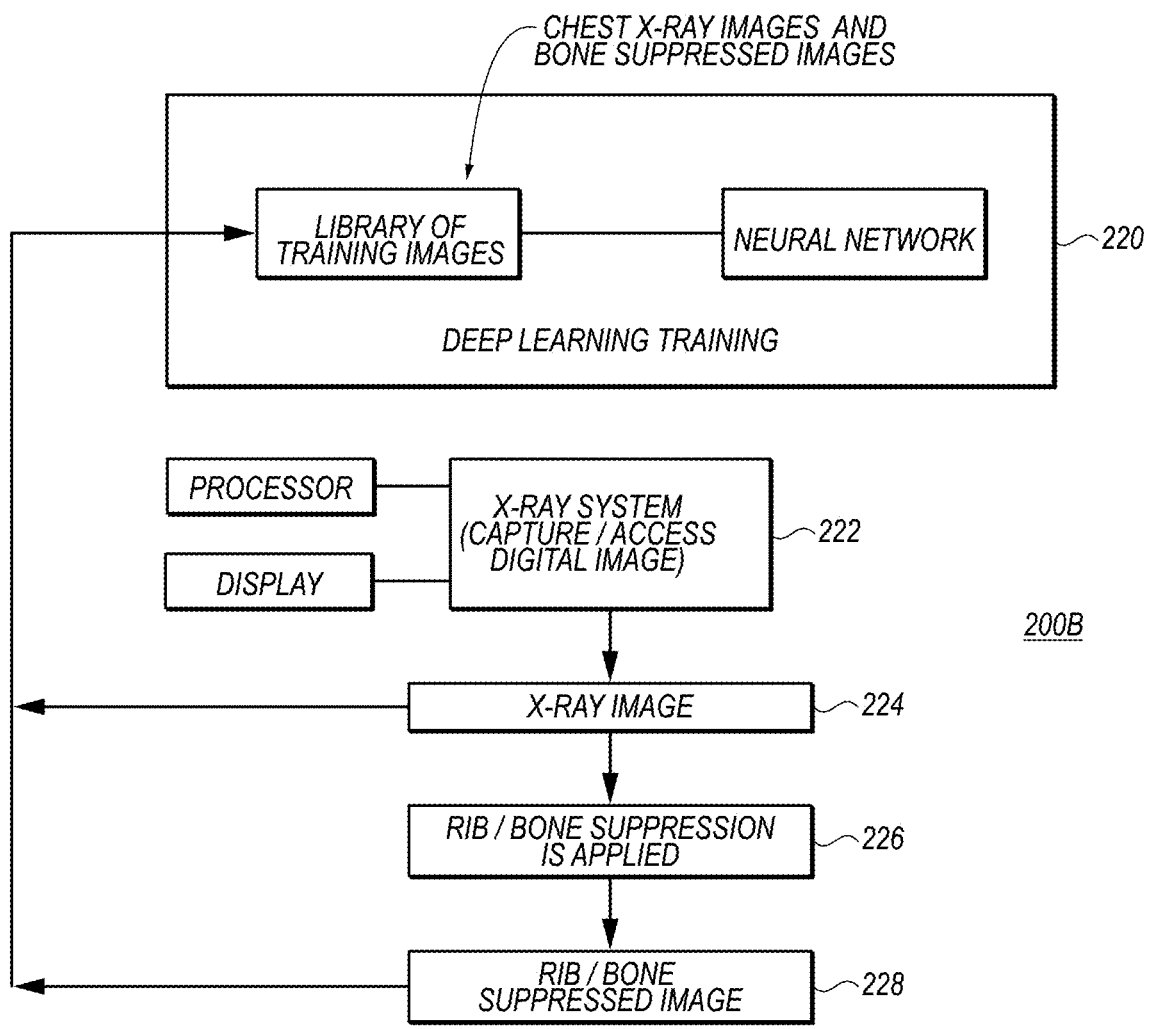

FIG. 2B illustrates an exemplary x-ray imaging system 200B, which may resemble the x-ray imaging system of FIG. 1 in certain respects, wherein a library of training images including pairs of original captured radiographic images and corresponding bone suppressed radiographic images, derived directly from the original captured radiographic images, are stored in digital electronic memory 220. The x-ray imaging system 200B also includes a neural network module stored in the digital electronic memory 220 which is available for training and for applying a learned bone suppression algorithm to radiographic images. The learned bone suppression algorithm may be applied to radiographic images captured by the x-ray imaging system 200B or to radiographic images captured elsewhere and provided to the x-ray imaging system 200B such as by providing access to electronic memory containing the radiographic images to be bone suppressed or by transmitting the radiographic images to the x-ray imaging system 200B. The neural network module may be trained using the library of training images. The x-ray imaging system 200B includes a processing system 222 having a processor, digital memory, and a display for displaying radiographic images. The processor may be programmable to store in the digital electronic memory radiographic images 224 captured by the x-ray imaging system 200B and to apply a conventional bone suppression algorithm 226, as disclosed in the patents incorporated herein by reference, to the stored radiographic images 224 to generate bone suppressed radiographic images 228. The processor may be programmed to store pairs of the captured radiographic images 224 and corresponding bone suppressed radiographic images 228 in the library of training images to be used by the neural network module for training.

Figure 2C:
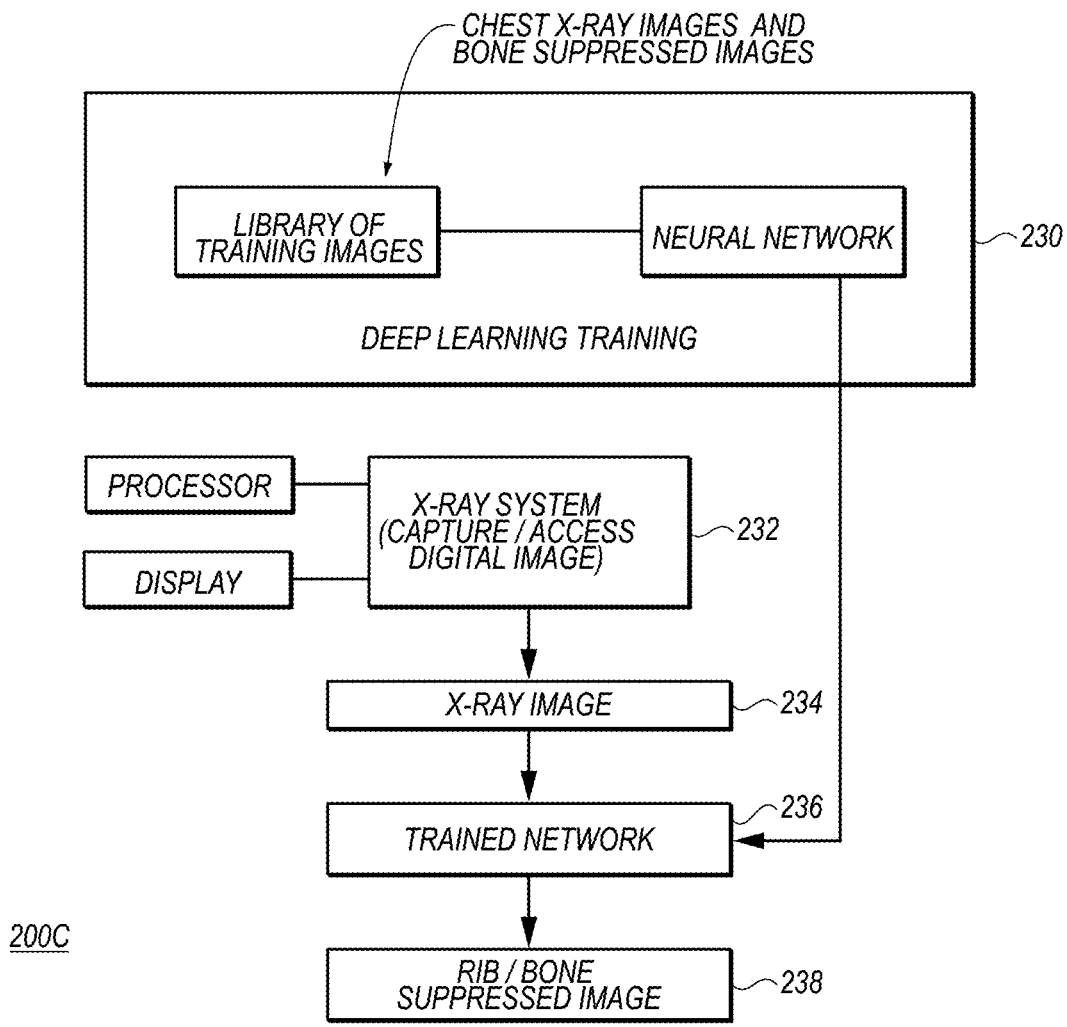

FIG. 2C illustrates an exemplary x-ray imaging system 200C, which may resemble the x-ray imaging system of FIG. 1 in certain respects, wherein a library of training images comprising pairs of original captured radiographic images and corresponding bone suppressed radiographic images, derived directly from the original captured radiographic images, are stored in digital electronic memory 230. The x-ray imaging system 200C also includes a neural network module stored in the digital electronic memory 230 which is available for being trained using the library of training images and for applying a learned bone suppression algorithm to radiographic images. The learned bone suppression algorithm may be applied to radiographic images captured by the x-ray imaging system 200C or to radiographic images captured elsewhere and provided to the x-ray imaging system 200C such as by providing access to electronic memory containing the radiographic images to be bone suppressed or by transmitting the radiographic images to the x-ray imaging system 200C. The neural network module may be trained using the library of training images. The x-ray imaging system 200C includes a processing system 232 having a processor, digital memory, and a display for displaying radiographic images. The processor may be programmable to provide a radiographic image 234 to the neural network after it's trained 236 so that the neural network generates a bone suppressed image by applying its trained bone suppression programming to the radiographic image to generate a neural network bone suppressed radiographic image 238.

Figure 2D:
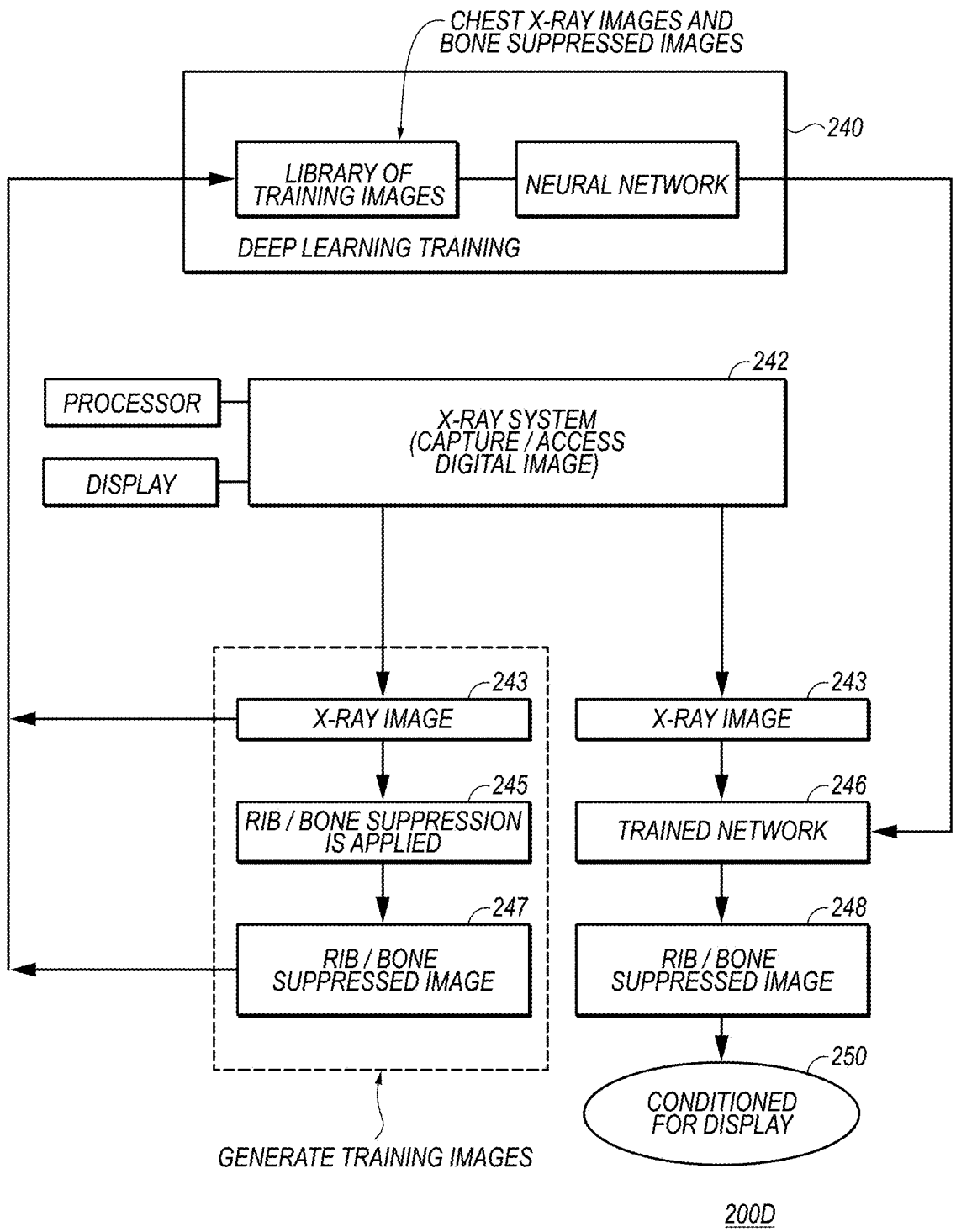

FIG. 2D illustrates an exemplary x-ray imaging system 200D, which may resemble the x-ray imaging system of FIG. 1 in certain respects, and may be operated according to the methods described with reference to both FIGS. 2B and 2C. The imaging system 200D includes a library of training images comprising pairs of original captured radiographic images and corresponding bone suppressed radiographic images, derived directly from the original captured radiographic images, stored in digital electronic memory 240.

The x-ray imaging system 200D also includes a neural network module stored in the digital electronic memory 240 which is available for training and for applying a learned bone suppression algorithm to radiographic images. The learned bone suppression algorithm may be applied to radiographic images captured by the x-ray imaging system 200D or to radiographic images captured elsewhere and provided to the x-ray imaging system 200D such as by providing access to electronic memory containing the radiographic images to be bone suppressed or by transmitting the radiographic images to the x-ray imaging system 200D. The neural network module may be trained using the library of training images. The x-ray imaging system 200D includes a processing system 242 having a processor, digital memory, and a display for displaying radiographic images. The processor may be programmable to store in the digital electronic memory 240 radiographic images 243 captured by the x-ray imaging system 200D and to apply a conventional bone suppression algorithm 245, as disclosed in the patents incorporated herein by reference, to the stored radiographic images 243 to generate bone suppressed radiographic images 247. The processor may be programmed to store pairs of the captured radiographic images 243 and corresponding bone suppressed radiographic images 247 in the library of training images to be used by the neural network module for training. Thus, the library of training images is supplied by use of the x-ray imaging system 200D. The processor may further be programmable to provide the radiographic image 243 to the neural network after it's trained 246 so that the neural network generates a bone suppressed image by applying its trained bone suppression programming to the radiographic image provided by the processor to generate a neural network bone suppressed radiographic image 248 which may then further be conditioned as necessary for display 250.

Figure 3:
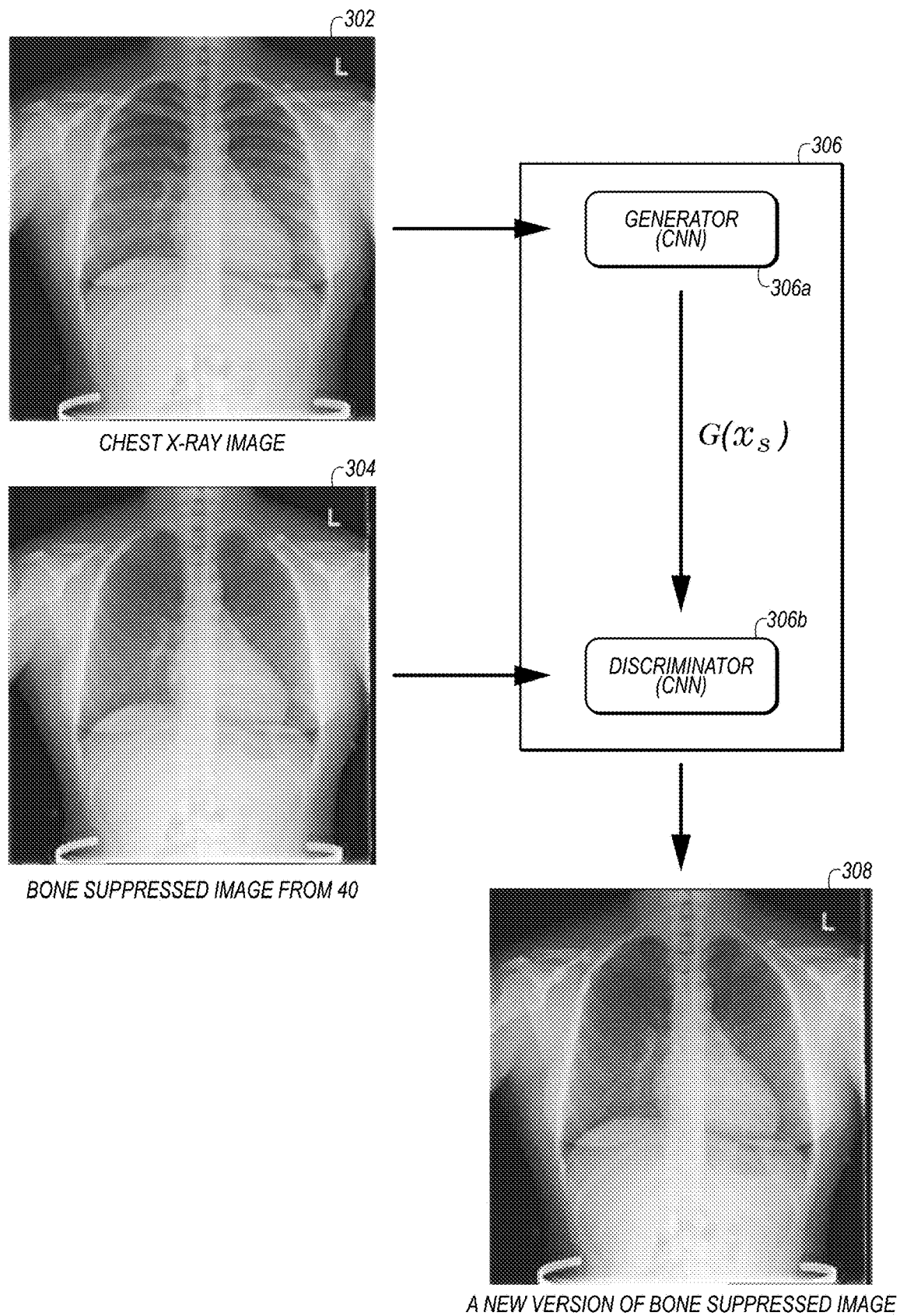
FIG. 3 is a flowchart in accordance with the present disclosure.
Figure 4:
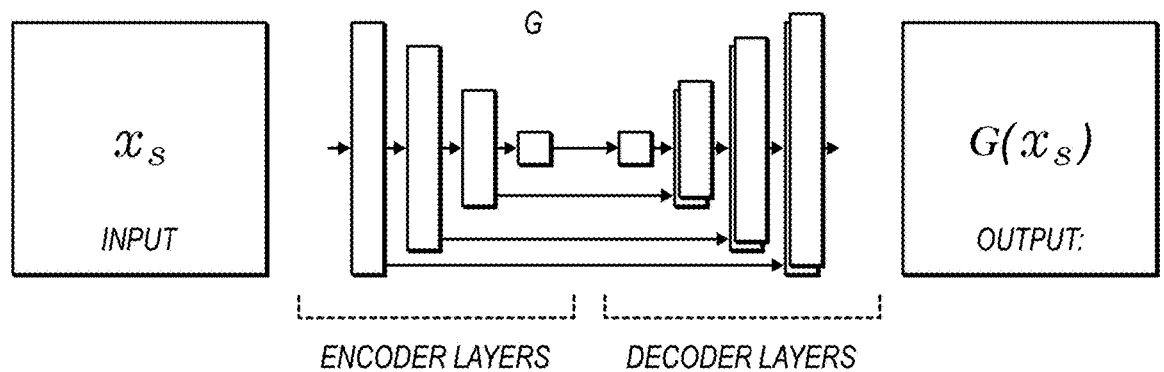
FIG. 4 illustrates the generator illustrated in FIG. 3.
Figure 5:
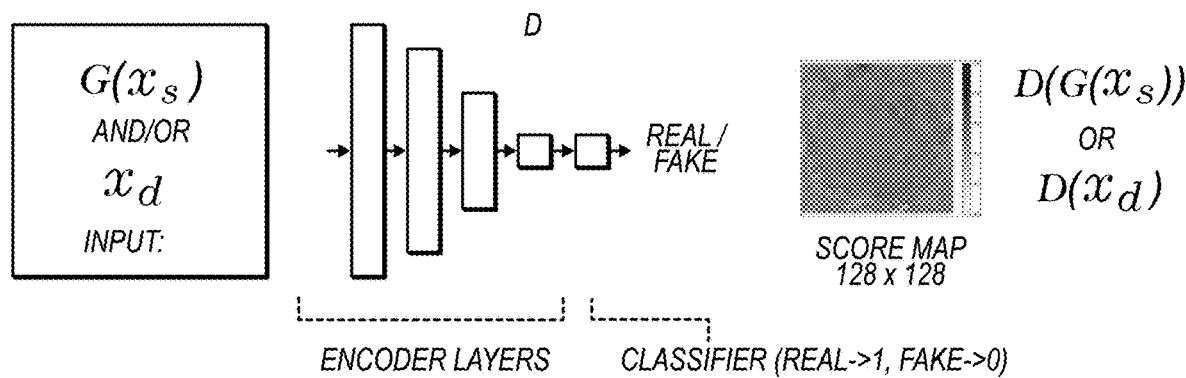
FIG. 5 illustrates the discriminator illustrated in FIG. 3.

FIGS. 3-5 illustrate a known GANs type neural network module 306 that may be trained to generate enhanced bone suppressed radiographic images using non-bone suppressed radiographic images as inputs. The neural network module 306 includes a generator 306a and discriminator 306b illustrated in FIGS. 4 and 5, respectively. In a training scheme, the GANs type neural network module 306 may be said to iteratively execute an optimization process by receiving a chest x-ray image 302 at the generator 306a and repeatedly attempting to generate a rib-suppressed x-ray image as an output to a discriminator 306b. The discriminator 306b receives the generator 306a generated image and a target bone suppressed image 304 which was generated from the chest x-ray image 302 using a known bone suppression algorithm. The discriminator compares the generator 306a generated x-ray image with the target x-ray image and scores the generator 306a generated image. The generator 306a uses the scoring data, in a known back propagation method, to repeatedly adjust a weighting scheme for image generation in the generator 306a until the generator's bone suppressed image output to the discriminator 306b is determined by the discriminator 306b to be acceptable, such as image 308, by satisfying a scoring threshold. FIG. 4 is a schematic diagram of a known mapping function carried out by the generator 306a, wherein the generator 306a receives a chest x-ray image $x_s$ and generates, via a network of encoding and decoding layers, a bone suppressed image $G(x_s)$. FIG. 5 is a schematic diagram of a known discriminator 306b that scores a comparison between the bone suppressed image from the generator 306a $G(x_s)$ and the target bone suppressed image $x_d$. The generator 306a may continue to adjust the generated bone suppressed images until a threshold acceptable score from the discriminator 306b is achieved, whereby the neural network may be considered to have completed training. The generator/discriminator may cooperate using two dimensional segments of the generated bone suppressed image $G(x_s)$ rather than on an entire frame of data. In one embodiment, the discriminator 306b may be programmed to estimate whether bone suppressed image data $G(x_s)$ provide by generator 306a was generated by the generator 306a or whether it originated from the target image $x_d$ as part of the discriminator 306b scoring scheme. This type of scoring may be said to comprise a contest between the generator 306a and discriminator 306b.

Figure 6A:
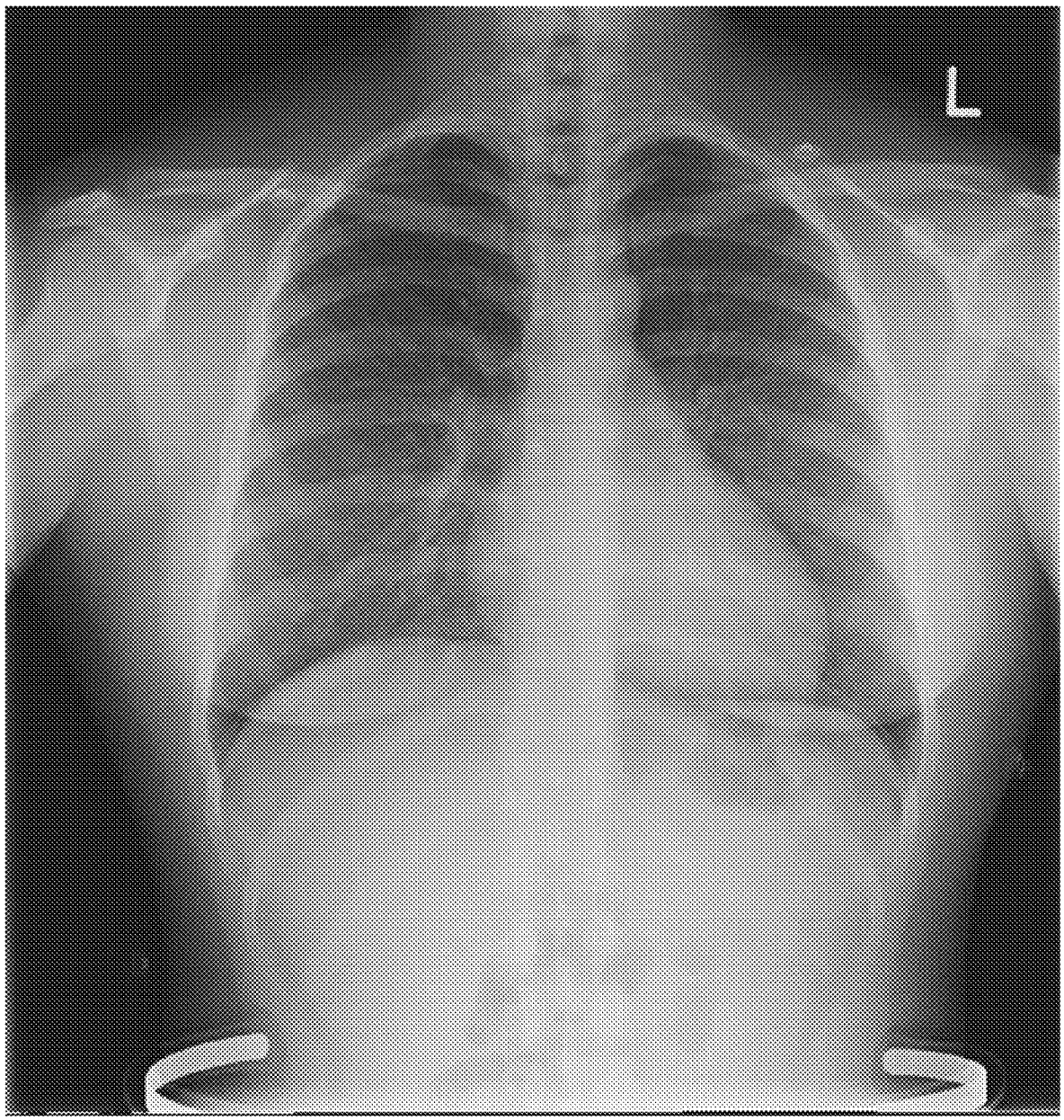
FIG. 6A is an exemplary chest x-ray image.
Figure 6B:
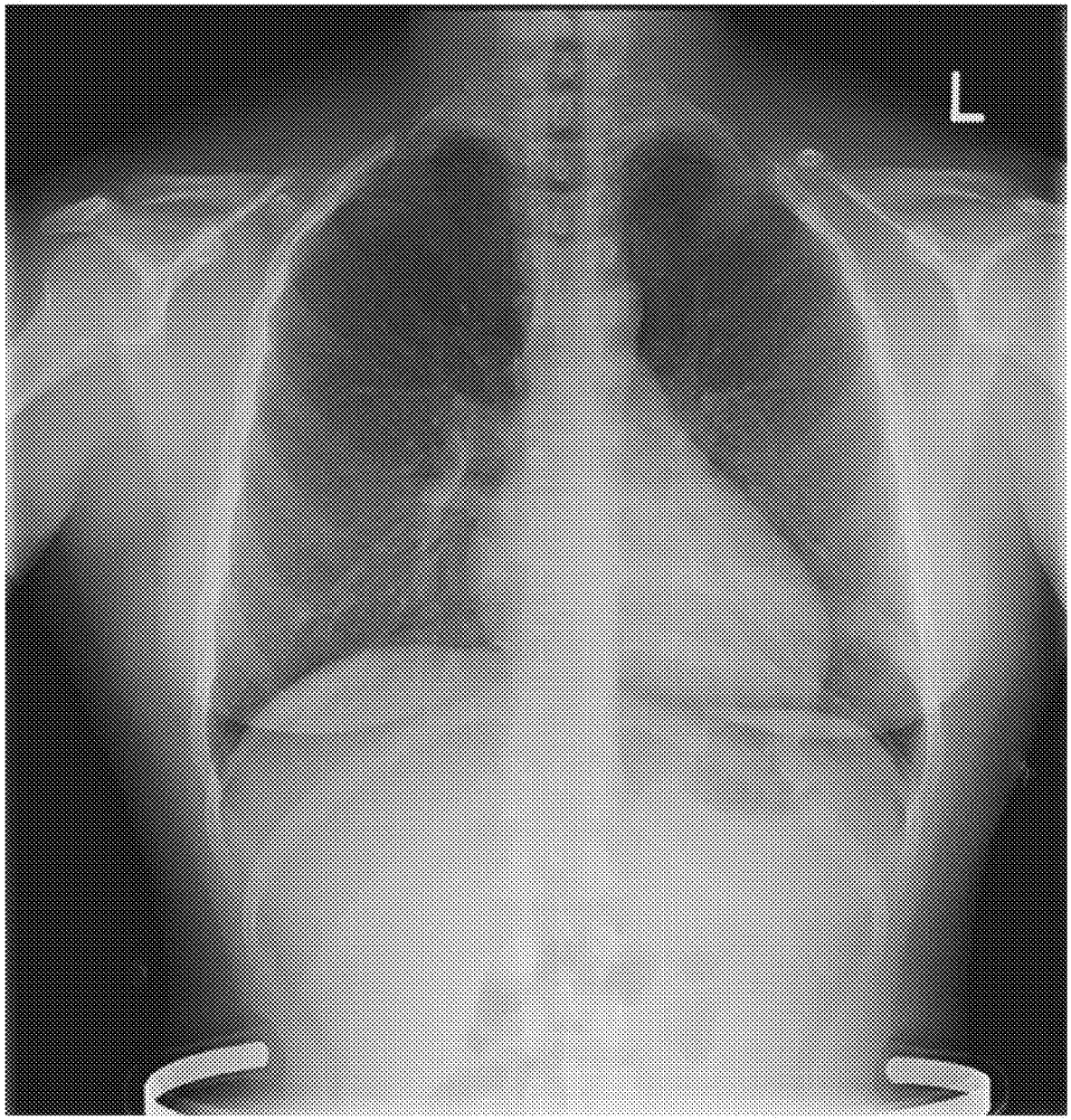
FIG. 6B is an exemplary rib suppressed image.
Figure 6C:
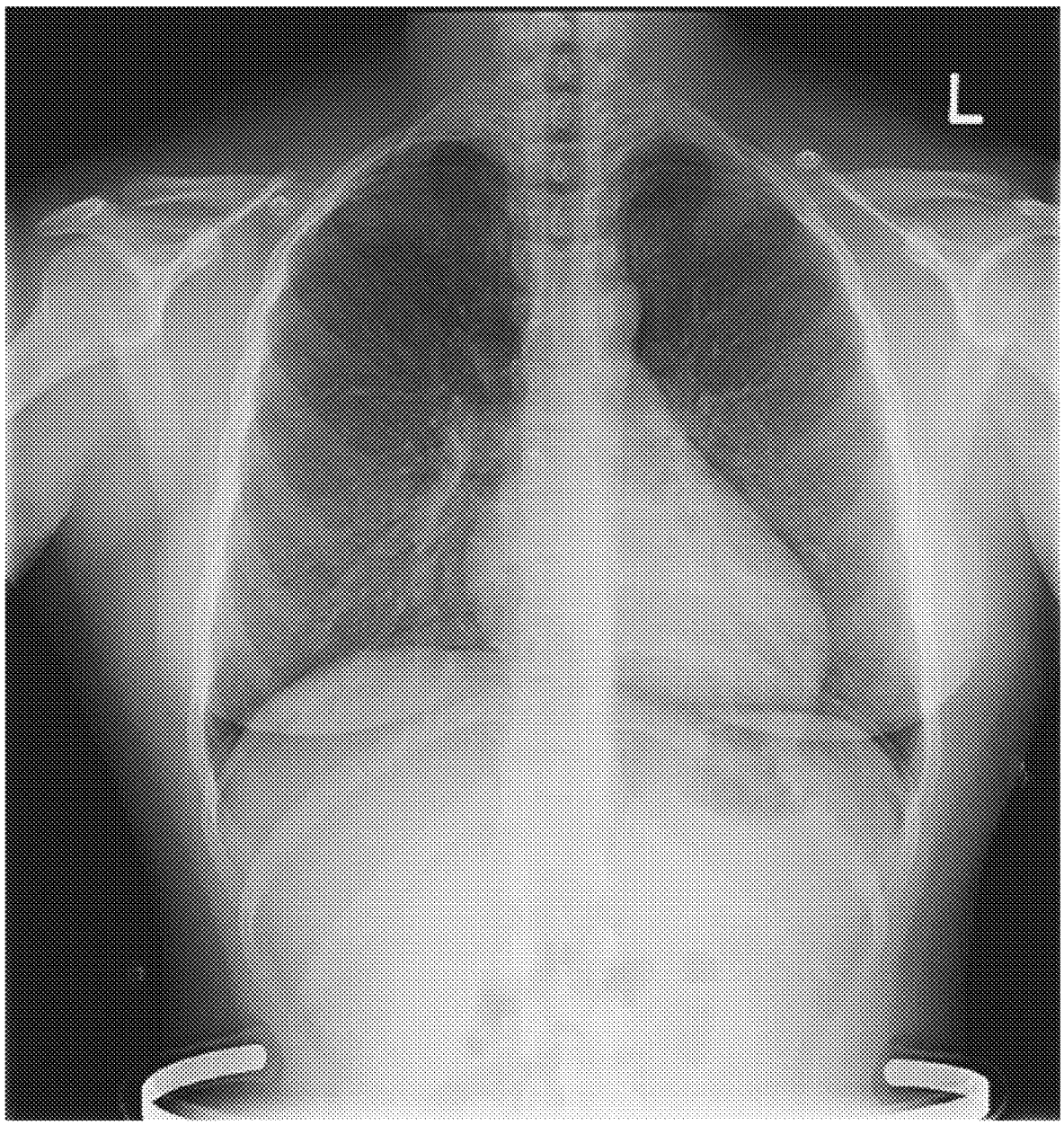
FIG. 6C is an exemplary enhanced bone suppressed image after the application of deep learning in accordance with the present disclosure.

FIGS. 6A-6C are exemplary radiographic images as described herein above. FIG. 6A is an exemplary original projection image (starting image) captured by a radiographic imaging system. FIG. 6B is an exemplary bone suppressed radiographic image version of FIG. 6A using the known bone suppression algorithms disclosed in the prior art patents incorporated herein by reference. FIG. 6C is an exemplary enhanced bone suppressed radiographic image generated by a trained neural network.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. Applicants have described a computer storage product having at least one computer storage medium having instructions stored therein causing one or more computers to perform the method described above. Applicants have described a computer storage medium having instructions stored therein for causing a computer to perform the method described above. Applicants have described a computer product embodied in a computer readable medium for performing the steps of the method described above.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system comprising:
    an x-ray source;
    an x-ray detector;
    a processor programmed to capture only one x-ray image of a patient, using the x-ray detector and only one exposure of the x-ray source, and to apply a bone suppression algorithm on the one captured x-ray image of the patient to generate a bone suppressed version of the one captured x-ray image of the patient, thereby forming a first radiographic image pair consisting of the one captured x-ray image and the bone suppressed version of the one captured x-ray image; and
    a deep learning module, wherein the processor is further programmed to train the deep learning module using the first radiographic image pair and a collection of additional radiographic image pairs each consisting of only one x-ray image captured with the detector using only one exposure of the x-ray source and a bone suppressed version thereof.

2. The system of claim 1, wherein the processor is configured to apply the trained deep learning module to a newly captured radiographic image of a patient to generate an enhanced bone suppressed version of the newly captured radiographic image of the patient.

3. A computer implemented method comprising:
    forming a plurality of radiographic image pairs each comprising a starting image and a target image, the plurality of radiographic image pairs each formed by the steps of:
    capturing only one digital radiographic image of a patient to form the starting image; and
    applying a bone suppression algorithm to the one captured digital radiographic image of the patient to form the target image; and
    providing a convolutional neural network module and training the module using the plurality of radiographic image pairs.

4. The method of claim 3, wherein the step of capturing includes capturing only one chest digital radiographic image, and wherein the step of applying includes forming a rib-suppressed target image.

5. The system of claim 1, wherein the processor is programmed to capture only one new x-ray image of a patient, using the x-ray detector and only one exposure of the x-ray source, to apply a bone suppression algorithm on the one new captured x-ray image of the patient to generate a bone suppressed version thereof, and to apply the trained deep learning module to the bone suppressed version to generate an enhanced bone suppressed version of the new captured x-ray image of the patient.

6. The method of claim 3, further comprising capturing a new digital x-ray image of a patient and applying the convolutional neural network module to the new digital x-ray image of a patient to generate an enhanced bone suppressed radiographic image of the patient.

7. The method of claim 3, further comprising capturing a new digital x-ray image of a patient, applying a bone suppression algorithm to the new digital x-ray image of the patient to generate a bone-suppressed digital x-ray image of the patient, and applying the convolutional neural network module to the bone suppressed digital x-ray image of the patient to generate an enhanced bone suppressed radiographic image of the patient.

* * * * *